United States Patent
Chanduszko

(10) Patent No.: US 8,029,529 B1
(45) Date of Patent: Oct. 4, 2011

(54) RETRIEVABLE FILTER

(75) Inventor: Andrzej J. Chanduszko, Chandler, AZ (US)

(73) Assignee: C. R. Bard, Inc., Murray Hill, NJ (US)

( * ) Notice: Subject to any disclaimer, the term of this patent is extended or adjusted under 35 U.S.C. 154(b) by 230 days.

(21) Appl. No.: 12/336,454

(22) Filed: Dec. 16, 2008

Related U.S. Application Data

(62) Division of application No. 11/334,829, filed on Jan. 19, 2006, now abandoned.

(60) Provisional application No. 60/645,347, filed on Jan. 19, 2005.

(51) Int. Cl.
*A61M 29/00* (2006.01)

(52) U.S. Cl. ........................................ 606/200

(58) Field of Classification Search .................. None
See application file for complete search history.

(56) References Cited

U.S. PATENT DOCUMENTS

| | | | |
|---|---|---|---|
| 893,055 A * | 7/1908 | Conner ................ | 81/3.41 |
| 5,300,086 A | 4/1994 | Gory et al. | |
| 5,350,398 A | 9/1994 | Pavcnik et al. | |
| 5,370,657 A * | 12/1994 | Irie .......................... | 606/200 |
| 5,531,788 A | 7/1996 | Dibie et al. | |
| 5,626,605 A * | 5/1997 | Irie et al. ................ | 623/1.1 |
| 5,720,764 A | 2/1998 | Naderlinger | |
| 5,836,968 A * | 11/1998 | Simon et al. ............. | 606/200 |
| 5,836,969 A | 11/1998 | Kim et al. | |
| 5,954,741 A | 9/1999 | Fox | |
| 6,059,825 A | 5/2000 | Hobbs et al. | |
| 6,080,178 A | 6/2000 | Meglin | |
| 6,126,673 A | 10/2000 | Kim et al. | |
| 6,231,589 B1 * | 5/2001 | Wessman et al. ......... | 606/200 |
| 6,251,122 B1 * | 6/2001 | Tsukernik ................. | 606/200 |
| 6,258,026 B1 * | 7/2001 | Ravenscroft et al. ..... | 600/200 |
| 6,267,776 B1 | 7/2001 | O'Connell | |
| 6,287,332 B1 | 9/2001 | Bolz et al. | |
| 6,306,163 B1 * | 10/2001 | Fitz .......................... | 623/1.12 |
| 6,391,045 B1 | 5/2002 | Kim et al. | |
| 6,436,120 B1 | 8/2002 | Meglin | |
| 6,447,530 B1 * | 9/2002 | Ostrovsky et al. ........ | 606/200 |
| 6,468,290 B1 | 10/2002 | Weldon et al. | |
| 6,517,573 B1 * | 2/2003 | Pollock et al. ............ | 623/1.15 |
| 6,540,767 B1 * | 4/2003 | Walak et al. .............. | 606/200 |
| 6,558,404 B2 * | 5/2003 | Tsukernik ................. | 606/198 |
| 6,582,447 B1 | 6/2003 | Patel et al. | |
| 6,652,558 B2 | 11/2003 | Patel et al. | |
| 6,682,540 B1 * | 1/2004 | Sancoff et al. ............ | 606/153 |
| 6,706,054 B2 * | 3/2004 | Wessman et al. ......... | 606/200 |
| 7,001,424 B2 | 2/2006 | Patel et al. | |
| 7,011,094 B2 * | 3/2006 | Rapacki et al. ........... | 128/207.15 |
| 7,033,376 B2 * | 4/2006 | Tsukernik ................. | 606/200 |
| 7,041,117 B2 | 5/2006 | Suon et al. | |
| 7,147,649 B2 | 12/2006 | Thomas | |
| 7,799,049 B2 * | 9/2010 | Ostrovsky et al. ........ | 606/200 |
| 2002/0004060 A1 | 1/2002 | Heublein et al. | |
| 2002/0138097 A1 * | 9/2002 | Ostrovsky et al. ........ | 606/200 |
| 2004/0158267 A1 * | 8/2004 | Sancoff et al. ............ | 606/153 |
| 2005/0288703 A1 | 12/2005 | Beyer et al. | |

(Continued)

*Primary Examiner* — Darwin Erezo
*Assistant Examiner* — Dianne Dornbusch
(74) *Attorney, Agent, or Firm* — Rutan & Tucker, LLP

(57) ABSTRACT

A vessel filter including a plurality of struts forming a first collapsible cone expanding radially outward in a proximal direction and a second collapsible cone expanding radially outward in a distal direction. A slidable member is disposed over the plurality of struts to collapse the struts toward a longitudinal axis of the vessel filter.

15 Claims, 10 Drawing Sheets

U.S. PATENT DOCUMENTS

| | | |
|---|---|---|
| 2005/0288704 A1 | 12/2005 | Cartier et al. |
| 2006/0004402 A1 | 1/2006 | Voeller et al. |
| 2006/0015137 A1 | 1/2006 | WasDyke et al. |
| 2006/0036279 A1 | 2/2006 | Eidenschink et al. |
| 2006/0041271 A1 | 2/2006 | Bosma et al. |
| 2006/0069405 A1 | 3/2006 | Schaeffer et al. |
| 2006/0069406 A1 | 3/2006 | Hendriksen et al. |
| 2006/0079928 A1 | 4/2006 | Cartier et al. |
| 2006/0079930 A1 | 4/2006 | McGuckin, Jr. et al. |
| 2006/0095068 A1 | 5/2006 | WasDyke et al. |
| 2006/0203769 A1 | 9/2006 | Saholt et al. |
| 2006/0206138 A1 | 9/2006 | Eidenschink |
| 2006/0259067 A1 | 11/2006 | Welch et al. |
| 2006/0259068 A1 | 11/2006 | Eidenschink |
| 2007/0005095 A1 | 1/2007 | Osborne et al. |
| 2007/0005104 A1 | 1/2007 | Kusleika et al. |
| 2007/0005105 A1 | 1/2007 | Kusleika et al. |

* cited by examiner

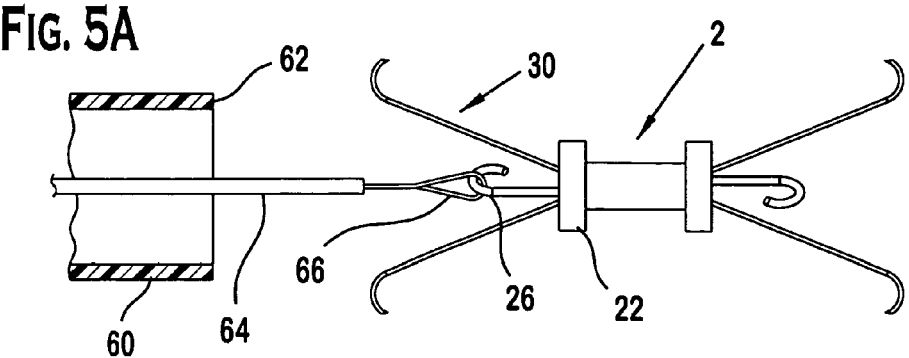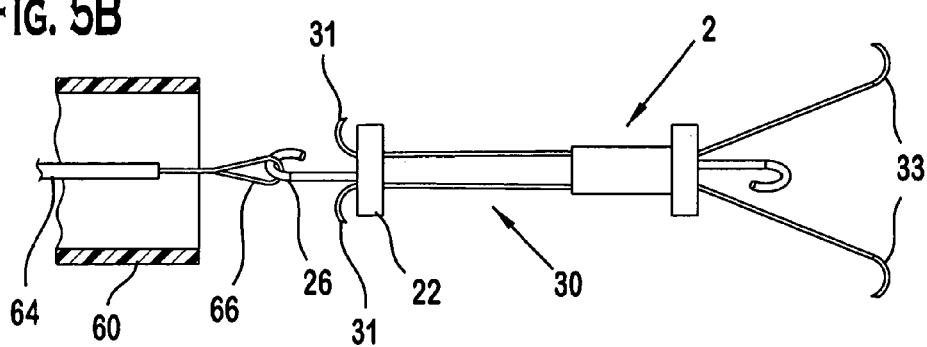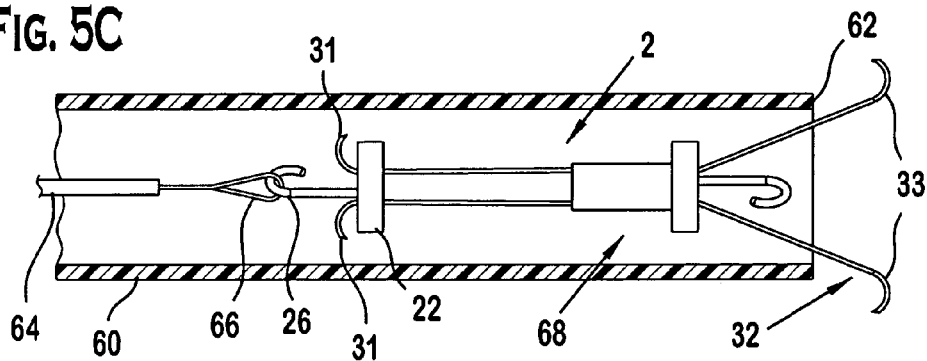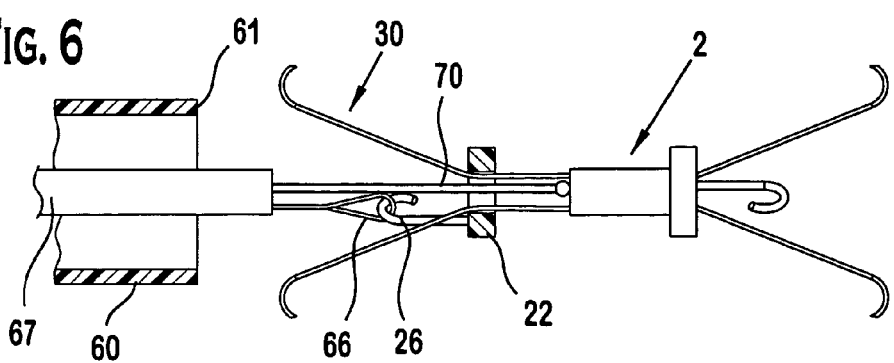

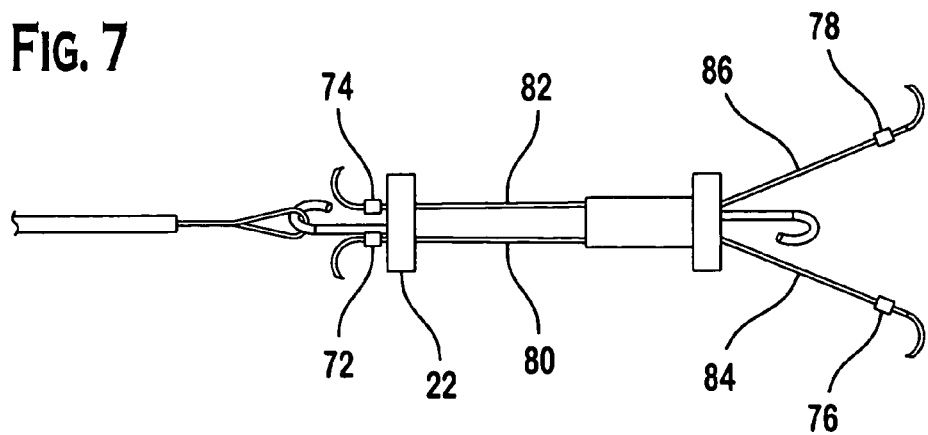
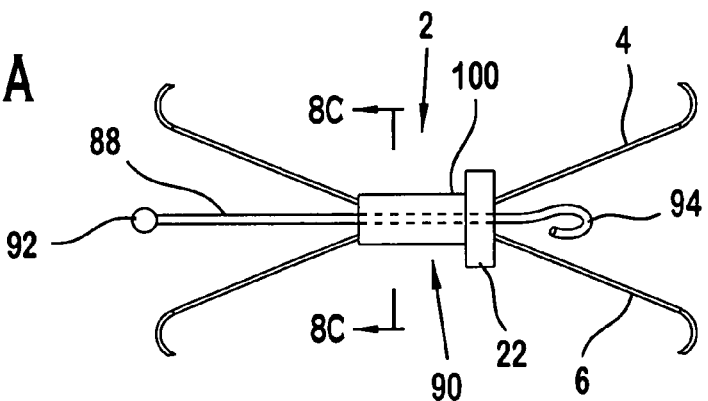
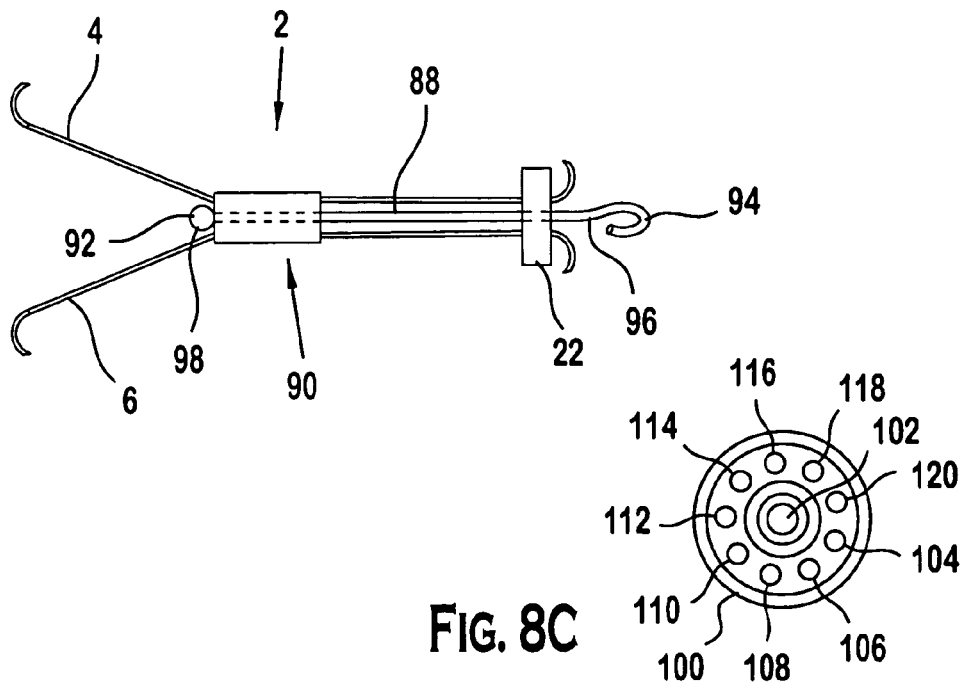

RETRIEVABLE FILTER

RELATED APPLICATIONS

This application is a divisional of U.S. patent application Ser. No. 11/334,829, filed Jan. 19, 2006, now abandoned, which claims the benefit of U.S. Provisional Patent Application No. 60/645,347, filed Jan. 19, 2005, each of which is incorporated by reference in its entirety herein.

BACKGROUND OF THE INVENTION

A vessel filter is a device inserted into a blood vessel to capture particles in the blood flow. Typically the device is inserted into a major vein to prevent a blood clot from reaching the lungs. Patients, who have recently suffered from trauma, have experienced a heart attack (myocardial infarction), or who have undergone major surgical procedure (e.g., surgical repair of a fractured hip, etc.) may have thrombosis in a deep vein. When the thrombus clot loosens from the site of formation and travels to the lung, it may cause pulmonary embolism, a life-threatening condition. A vessel filter may be placed in the circulatory system to intercept the thrombi and prevent them from entering the lungs.

Examples of various blood vessel filters and delivery systems are disclosed in U.S. Pat. No. 5,300,086, titled "DEVICE WITH A LOCATING MEMBER FOR REMOVABLY IMPLANTING A BLOOD FILTER IN A VEIN OF THE HUMAN BODY" issued to Gory et al., dated Apr. 5, 1994; U.S. Pat. No. 5,350,398, titled "SELF-EXPANDING FILTER FOR PERCUTANEOUS INSERTION" issued to Pavcnik et al., dated Sep. 27, 1994; U.S. Pat. No. 5,531,788, titled "ANTI-PULMONARY EMBOLISM FILTER" issued to Dibie et al., dated Jul. 2, 1996; U.S. Pat. No. 5,720,764, titled "VENA CAVA THROMBUS FILTER" issued to Naderlinger, dated Feb. 24, 1998; U.S. Pat. No. 5,836,969, titled "VENA CAVA FILTER" issued to Kim et al., dated Nov. 17, 1998; U.S. Pat. No. 5,954,741 titled "VENA-CAVA FILTER" issued to Fox, dated Sep. 21, 1999; U.S. Pat. No. 6,059,825, titled CLOT FILTER issued to Hobbs et al., dated May 9, 2000; U.S. Pat. No. 6,126,673, titled "VENA CAVA FILTER" issued to Kim et al., dated Oct. 3, 2000; U.S. Pat. No. 6,080,178, titled "VENA CAVA FILTER" issued to Meglin, dated Jun. 27, 2000; U.S. Pat. No. 6,251,122 B1, titled "INTRAVASCULAR FILTER RETRIEVAL DEVICE AND METHOD" issued to Tsukernik, dated Jun. 26, 2001; U.S. Pat. No. 6,258,026 B1, titled "REMOVEABLE EMBOLUS BLOOD CLOT FILTER DELIVERY UNIT" issued to Ravenscroft et al., dated Jul. 10, 2001; U.S. Pat. No. 6,391,045 B1, titled "VENA CAVA FILTER" issued to Kim et al., dated May 21, 2002; U.S. Pat. No. 6,436,120 B1, titled "VENA CAVA FILTER" issued to Meglin, dated Aug. 20, 2002; U.S. Pat. No. 6,468,290 B1, titled "TWO-PLANAR VENA CAVA FILTER WITH SELF-CENTERING CAPABILITIES" issued to Weldon et al., dated Oct. 22, 2002; U.S. Pat. No. 6,582,447 B1, titled "CONVERTIBLE BLOOD CLOT FILTER" issued to Patel et al., dated Jun. 24, 2003; U.S. Pat. No. 6,652,558 B2, titled "CONVERTIBLE BLOOD CLOT FILTER" issued to Patel et al., dated Nov. 25, 2003; each of which is incorporated herein by reference in its entirety.

Typically, the filter includes a plurality of radially expandable legs that support one or more filter baskets having a conical configuration. The device is configured for compression into a small size to facilitate delivery into a vascular passageway and is subsequently expanded into contact with the inner wall of the vessel. The device may later be retrieved from the deployed site by compressing the radially expanded legs and the associated baskets back into a small size for retrieval. The radially expandable legs may further include engagements for anchoring the filter in position within a blood vessel (e.g., vena cava). For example, the expandable legs may have hooks that can penetrate into the vessel wall and positively prevent migration of the filter in either direction along the length of the vessel. The body of the filter may include various biocompatible materials including compressible spring metals and shape memory materials to allow easy expansion and compression of the filter within the vessel. The hooks on the radially expandable legs may further include materials more elastic than the legs to permit the hooks to straighten in response to withdrawal forces to facilitate withdrawal from the endothelium layer without risk of significant injury to the vessel wall. The hooks may be formed on selected radially expandable legs, but not on others.

Many of the existing vena cava filters routinely encounter problems during retrieval. In addition, typical filters' deployment and retrieval are directionally dependent. For example, filters inserted using a femoral approach may require the retrieval to take place through a jugular approach. Accordingly, applicants recognize the desirability of a vena cava filter that can be easily retrieved independent of the orientation of the filter deployment within the vessel.

BRIEF SUMMARY OF THE INVENTION

Described herein is a vessel filter with an integrated mechanism for compressing vessel filter legs and facilitating retrieval of the vessel filter. In one embodiment, the vessel filter includes a plurality of struts forming two cones at the proximal and the distal ends. The struts are coupled together at the mid-sections thereof. Hooks may extend from the ends of the struts for engaging the blood vessel wall. The struts are threaded through two slidable members. The slidable members may include rings that are slidably disposed along the length of the struts. The two rings may be connected to each other to prevent detachment from the struts. Retrieval members may be coupled to the slidable members to allow the user to engage the slidable members and collapse the struts. To retrieve the deployed vessel filter, the physician first engages one of the slidable members and collapses the corresponding expanded cone. Once the first cone is collapsed, a recovery sheath or catheter can be advanced over the collapsed cone. The second expanded cone at the opposite side of the vessel filter is collapsed as the recovery sheath is advanced over the entire length of the vessel filter. Once the entire vessel filter is positioned within the lumen of the recovery sheath, the recovery sheath along with the captured vessel filter is withdrawn from the body of the patient.

In another embodiment, the slidable member includes an elongated tubular body which includes a plurality of slots to allow a portion of the struts, the struts forming the legs of the filter, to pass through the circumferential wall of the tubular body. The displacement of the tubular body relative to the struts forces the segments of struts extending through the slots to collapse toward a longitudinal axis of the vessel filter. A retrieval member may be provided on the tubular body to allow the user to engage the tubular body. For example, a flexible rod with an engagement interface (e.g., a snare, etc.) at the distal end of the rod may be inserted through a recovery sheath to engage the retrieval member. The user then retracts the rod and forces the tubular body to displace toward the recovery sheath, collapsing the legs at the proximal end of the filter. Once the proximal legs of the filter have been compressed, the recovery sheath is advanced distally to compress the filter legs at the distal end of the filter to capture the entire vessel filter within the lumen of the recovery sheath.

In one embodiment, a vessel filter includes a plurality of struts, a slidable member disposed over the plurality of struts, the slidable member configured for sliding over the proximal portion of the plurality of struts to collapse the first collapsible cone, and a coupling member positioned over a mid-section of said plurality of struts, a proximal portion of the plurality of struts configured to form a first collapsible cone expanding radially from the coupling member in a proximal direction, a distal portion of the plurality of struts configured to form a second collapsible cone expanding radially from the coupling member in a distal direction. In another embodiment, an implantable vascular device includes a connecting member, a first compressible filter attached to a distal end of the connecting member, a second compressible filter attached to a proximal end of the connecting member, and a first slidable member disposed over the connecting member, the first slidable member configured to compress at least one of the first and second compressible filters when the first slidable member is positioned thereover.

In yet another embodiment, a vessel filter includes an elongated structure including a lumen, a proximal end, and a distal end, the elongated structure comprising a plurality of slots, and a plurality of struts slidably disposed within the lumen of the elongated structure, a proximal portion of the plurality of struts passing through a wall of the elongated structure through at least some of the plurality of slots and forming a first cone-shaped filter, a distal portion of the plurality of struts passing through the wall of the elongated structure through at least some of the plurality of slots and forming a second cone-shaped filter, the elongated structure slidable such that when slid in a proximal direction relative to the plurality of struts the first cone-shaped filter collapses toward a longitudinal axis of the vessel filter and when slid in a distal direction relative to the plurality of struts the second cone-shaped filter collapses toward the longitudinal axis of the vessel filter.

In still another embodiment, an implantable vascular device includes a first compressible filter including a proximal end and a distal end, the first compressible filter expanding radially away from the longitudinal axis from the proximal end toward the distal end, a second compressible filter including a proximal end and a distal end, the second compressible filter expanding radially away from the longitudinal axis from the distal end toward the proximal end, the proximal end of the first compressible filter coupled to the distal end of the second compressible filter, and means for compressing at least one of the two compressible filters. In another embodiment, an implantable vascular device, including a distal portion and a proximal portion includes means for filtering blood clots positioned at the proximal portion of the device, means for centering a distal end of the device positioned at the distal portion of the device, and means for compressing the means for filtering blood clots.

In one embodiment, a method for retrieving an implanted vascular device from a patient's body includes locating the implanted vascular device, the vascular device including a first compressible filter including a proximal end and a distal end, the first compressible filter expanding radially away from a longitudinal axis of the vascular device from the proximal end toward the distal end, a second compressible filter including a proximal end and a distal end, the second compressible filter expanding radially away from the longitudinal axis from the distal end toward the proximal end, the proximal end of the first compressible filter coupled to the distal end of the second compressible filter, and a slidable member disposed between the first and the second compressible filter, and engaging the slidable member to compress the first compressible filter.

In one embodiment, a blood vessel filter includes a first set of struts joined together at a joined end, the struts extending radially outward therefrom in a first direction, at least one of the first set of struts including a hook on a free end, the hook having a cross-sectional area less than a cross-sectional area of the strut, a second set of struts joined together at a joined end, the struts extending radially outward therefrom in a second direction different from the first direction, a first slidable member disposed at least partially over the coupling member, and a coupling member coupling the first set of struts to the second set of struts at the joined ends thereof.

These and other embodiments, features and advantages of the present invention will become more apparent to those skilled in the art when taken with reference to the following more detailed description of the invention in conjunction with the accompanying drawings that are first briefly described.

BRIEF DESCRIPTION OF THE DRAWINGS

FIGS. 5A-5C illustrate an exemplary approach for the retrieval of a vessel filter.

FIG. 5A shows a snare engaging the retrieval member on one of the slidable members.

FIG. 5B shows the slidable member being displaced by the snare, which forces the legs on the one proximal end of the vessel filter to collapse.

FIG. 5C shows the advancement of the recovery sheath to compress the legs at the distal end of the filter, and, as a result, capturing the entire vessel filter within the lumen of the recovery sheath.

FIG. 6 illustrates another variation of a recovery system, in which a restraining member is utilized to maintain the position of the vessel filter within the blood vessel while a slidable member is being displaced.

FIG. 7 illustrates another variation of a vessel filter with stoppers positioned at the distal portion of the filter legs to prevent the slidable member from dislodging from the legs of the vessel filter.

FIG. 8A illustrates another variation where the slidable member is configured with a stopper mechanism extending through the mid-portion of the filter structure. The stopper mechanism limits the lateral displacement of the slidable member and prevents the slidable member from disengaging from the filter legs.

FIG. 8B illustrates the vessel filter of FIG. 8A with the slidable member fully displaced to compress the legs at the distal end of the vessel filter.

FIG. 8C illustrates the cross-sectional view of the vessel filter of FIG. 8A. The cross-section is taken at "A-A" as shown in FIG. 8A.

DETAILED DESCRIPTION OF THE VARIOUS EMBODIMENTS

Figure 1A:
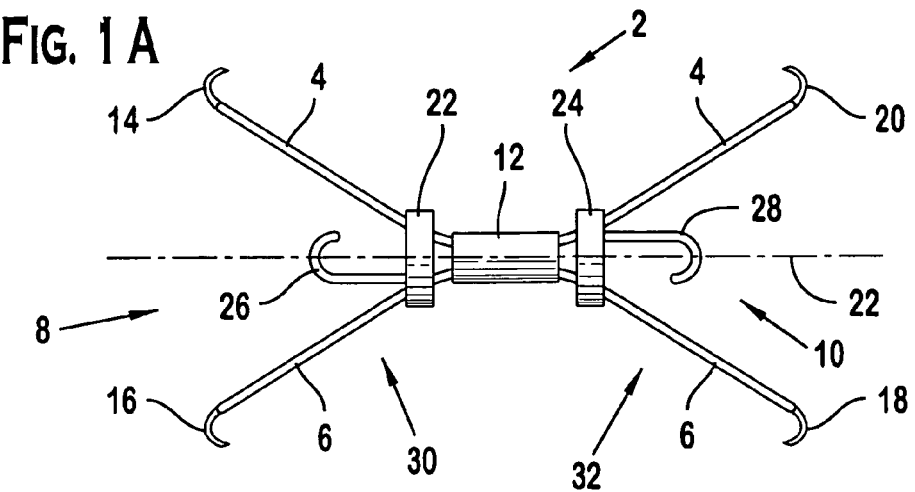
FIG. 1A illustrates one variation of a vessel filter with an integrated compression mechanism for filter recovery. The filter includes struts forming two cones at the distal and the proximal ends of the filter. Two slidable members are displaced over the struts to serve as the compression mechanism.

The following detailed description should be read with reference to the drawings, in which identical reference numbers refer to like elements through out the different figures. The drawings, which are not necessarily to scale, depict selected embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

Before describing the present invention, it is to be understood that unless otherwise indicated, this invention need not be limited to applications in humans. As one of ordinary skill in the art would appreciate, variations of the invention may be applied to other mammals as well. Moreover, it should be understood that embodiments of the present invention may be applied in combination with various catheters, guidewires, tubing introducers or other filter deployment devices for implantation of a filter in a vessel within a patient's body.

Implantation of the filter within the vena cava is used herein as an example application of the filter device to illustrate the various aspects of the invention disclosed herein. In light of the disclosure herein, one skilled in the art would appreciate that variations of the filter may be applicable for placement in various blood vessels, hollow body organs or elongated cavities in a human body. It is also contemplated that the vessel filter described herein may be implemented for capturing particles other than blood clots.

It must also be noted that, as used in this specification and the appended claims, the singular forms "a," "an" and "the" include plural referents unless the context clearly dictates otherwise. Thus, for example, the term "a hook" is intended to mean a single hook or a combination of hooks, "a fluid" is intended to mean one or more fluids, or a mixture thereof.

As used herein, the term "hook" means a member configured to engage a blood vessel wall, examples of which are provided in U.S. Pat. No. 6,258,026, which is incorporated by reference as if fully set forth herein. Moreover, as used herein, the term "suture material" means a material that is, or could be, used as a suture thread by a surgeon, including, for example, synthetic polymers, polyglycolic acid (PGA), polylactic acid (PLA), polydioxanone (PDS), polyglactin, nylon, polypropylene (prolene), silk, catgut, non-absorbable/non-biodegradable materials, and combinations thereof. Included in this term are both monofilament and multifilament suture materials.

Further, as used herein, the term "bio-resorbable" includes a suitable biocompatible material, mixture of various biocompatible materials or partial components of biocompatible material being altered into other materials by an agent present in the environment (e.g., a biodegradable material that degrades via a suitable mechanism such as hydrolysis when placed in biological tissue); such materials being removed by cellular activity or incorporated into the cellular structure (i.e., bioresorption, bioresorping, bioabsorption, or bioresorbable), such materials being degraded by bulk or surface degradation (i.e., bioerosion such as, for example, a water insoluble polymer that turns water-soluble in contact with biological tissue or fluid), or such materials being altered by a combination of one or more of biodegradable, bioerodable or bioresorpable activity when placed in contact with biological tissue or fluid.

Possible materials for the filter and/or tube described herein include a suitable biocompatible material such as, for example, stainless steel, noble metals and their alloys, shape memory metals, shape memory alloys, super elastic metal, super elastic shape memory metal alloys, linear elastic shape memory metal, metal alloys, shape memory polymers, polymers, bio-resorbable materials (e.g., metal alloys such as those shown and described in U.S. Pat. No. 6,287,332; and U.S. Patent Application Publication No. 2002/0004060, which are incorporated by reference in their entireties into this application), and combinations thereof.

Where the filter is to be utilized with bio-active agents to control the formation of emboli, bio-active agents can be coated to a portion or the entirety of the filter for controlled release of the agents once the filter is implanted. The bio-active agents can include, but are not limited to, vasodilator, anti-coagulants, such as, for example, warfarin and heparin. Other bio-active agents can include, but are not limited to, agents such as, for example, anti-proliferative/antimitotic agents including natural products such as vinca alkaloids (i.e. vinblastine, vincristine, and vinorelbine), paclitaxel, epidipodophyllotoxins (i.e. etoposide, teniposide), antibiotics (dactinomycin (actinomycin D) daunorubicin, doxorubicin and idarubicin), anthracyclines, mitoxantrone, bleomycins, plicamycin (mithramycin) and mitomycin, enzymes (L-asparaginase which systemically metabolizes L-asparagine and deprives cells which do not have the capacity to synthesize their own asparagine); antiplatelet agents such as G(GP) II$_b$/III$_a$ inhibitors and vitronectin receptor antagonists; anti-proliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nirtosoureas (carmustine (BCNU) and analogs, streptozocin), trazenes—dacarbazinine (DTIC); anti-proliferative/antimitotic antimetabolites such as folic acid analogs (methotrexate), pyrimidine analogs (fluorouracil, floxuridine, and cytarabine), purine analogs and related inhibitors (mercaptopurine, thioguanine, pentostatin and 2-chlorodeoxyadenosine {cladribine}); platinum coordination complexes (cisplatin, carboplatin), procarbazine, hydroxyurea, mitotane, aminoglutethimide; hormones (i.e. estrogen); anti-coagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory; antisecretory (breveldin); anti-inflammatory: such as adrenocortical steroids (cortisol, cortisone, fludrocortisone, prednisone, prednisolone, 6α-methylprednisolone, triamcinolone, betamethasone, and dexamethasone), non-steroidal agents (salicylic acid derivatives i.e. aspirin; para-aminophenol derivatives i.e. acetominophen; indole and indene acetic acids (indomethacin, sulindac, and etodalac), heteroaryl acetic acids (tolmetin, diclofenac, and ketorolac), arylpropionic acids (ibuprofen and derivatives), anthranilic acids (mefenamic acid, and meclofenamic acid), enolic acids (piroxicam, tenoxicam, phenylbutazone, and oxyphenthatrazone), nabumetone, gold compounds (auranofin, aurothioglucose, gold sodium thiomalate); immunosuppressives: (cyclosporine, tacrolimus (FK-506), sirolimus (rapamycin), azathioprine, mycophenolate mofetil); angiogenic agents: vascular endothelial growth factor (VEGF), fibroblast growth factor (FGF); angiotensin receptor blockers; nitric oxide donors; anti-sense oligionucleotides and combinations thereof; cell cycle inhibitors, mTOR inhibitors, and growth factor receptor signal transduction kinase inhibitors; retenoids; cyclin/CDK inhibitors; HMG co-enzyme reductase inhibitors (statins); and protease inhibitors.

In one aspect of the invention, the vessel filter includes struts forming two expandable filter components at the distal and the proximal end of the device. A slidable member is disposed over the struts allowing the user to electively compress one of the expandable filter components such that the filter can be captured within a catheter and retrieved from the patient's body. The struts are sufficiently flexible in order to bend from an expanded position to a collapsed position for recovery of the vessel filter upon movement of the sliding member along a longitudinal axis of the vessel filter. The cross-sectional shape of the struts forming a filter component may be circular, elliptical, square, rectangular, triangular, or any other shape; however, the preferred shape is circular. The cross-sectional shape may be constant over the length of the strut or may be different along select sections of the struts. Moreover, the cross-sectional area of the struts may vary along the length thereof.

In one example, illustrated in FIG. 1A, the vessel filter 2 includes nitinol struts 4, 6 forming two cones 8, 10. In other variations the struts 4, 6 may include other materials, including, but not limited to, metals, metal alloys, shape memory materials, polymers, or biodegradable polymers. The vessel filter 2 may include three, four, five, six or more struts. To illustrate the functionality of the vessel filter 2 in FIG. 1A, the vessel filter is shown with only two of its struts. The tips of the struts may be configured with hooks 14, 16, 18, 20. The hooks 14, 16, 18, 20 may be configured with a predetermined resistance force such that a withdrawal force in excess of the predetermined resistance force causes the hooks to straighten and bend toward the longitudinal axis 22 of the vessel filter. One skilled in the art would appreciate that other hook configurations (e.g., elastic hooks, etc.) may also be implemented on the vessel filters described herein.

Figure 1B:
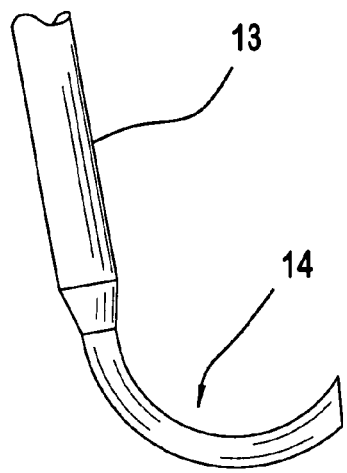
FIG. 1B is a side view of one embodiment of a hook for the vessel filter of FIG. 1A.
Figure 1C:
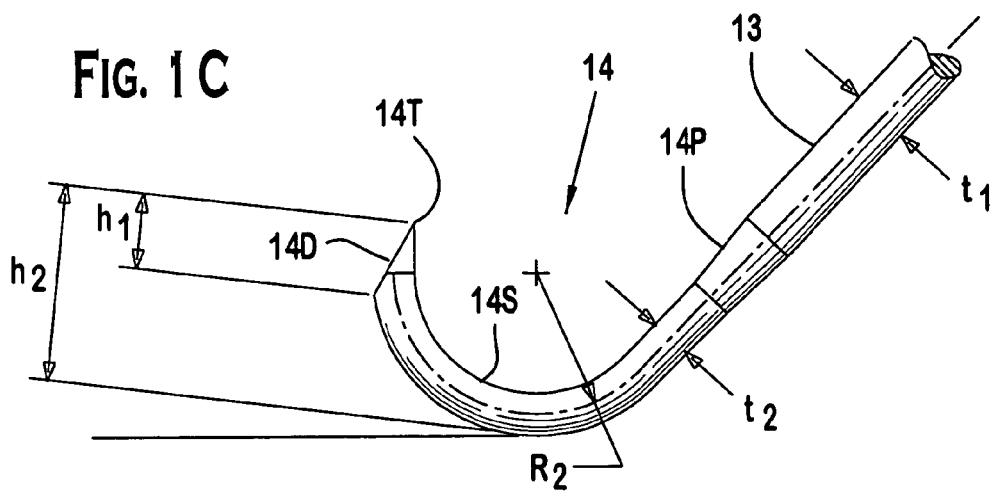
FIG. 1C is a side view of another embodiment of a hook for the vessel filter of FIG. 1A.

In one embodiment, the hooks 14, 16, 18, 20 are designed with an elastic structure that permits the hook to straighten, as shown in FIGS. 1B and 1C. An elastic structure as defined herein means that the hook 14 has a generally curved or arcuate configuration in an operative condition and a generally linear configuration in a constrained condition. Referring to FIG. 1B, hook 14 is shown attached to a shaft or leg section 13, the hook 14 having a cross-sectional area which is less than a cross-sectional area of the leg section 13 to facilitate removal and prevent the hook 14 from tearing the vessel wall during withdrawal. While the hook 14 in FIG. 1B is shown with a cross-sectional area throughout its length that is less than a cross-sectional area of the leg section 13, in other embodiments, one or more discrete sections of the hook 14 may be configured with cross-sectional areas less than a cross-sectional area of the leg section 13, while other discrete sections may be configured with cross-sectional areas that are equal to or greater than a cross-sectional area of the leg section 13. In one embodiment, shown in FIG. 1C, hook 14 has a proximal hook portion 14P and a distal hook portion on which a sharpened tip 14T is provided. Proximal hook portion 14P may have a thickness that decreases to a thickness t2 from the thickness t1 of leg section 13. In an embodiment in which the hook is formed from a wire having a generally circular cross-section, the thickness t2 is generally equal to the outside diameter of the wire. The wire can be configured to follow a radius of curvature R2. The tip 14T may include a generally planar surface 14D having a length approximately equal to length h1. The tip 14T is located over a distance h2 from a plane tangential to the curved portion 40S.

Referring to FIG. 1A, the struts 4, 6 are threaded through two slidable members 22, 24 and are connected in the middle with a coupling or connecting member, such as a welded tube 12 (e.g., welded nitinol tube). The coupling member acts to prevent the potential problem of struts twisting and/or crossing during implantation and/or recovery procedures. For example, in vessel filters of this type without a coupling member, implantation of the vessel filter may cause the struts to twist and cross one another because they are not firmly established in their preset configuration. As a result, the proper deployment of the filter may be prevented, leading to potential complications. By including a coupling member, the vessel filter 2 is permitted to correctly deploy within a blood vessel, the coupling member maintaining the struts in their preset configuration with respect to one another. The potential problem of struts twisting and/or crossing to prevent expected and correct implantation of the vessel filter is thereby avoided through use of the coupling member in certain embodiments described herein.

In the embodiment shown in FIG. 1A, each of the slidable members 22, 24 includes a ring that can be displaced along the length of the struts. The two slidable members 22, 24 may be connected together to prevent detachment from the filter structure. Each slidable member 22, 24 is further configured with a retrieval member 26, 28 coupled to the body of the slidable member. In one variation, the vessel filter 2 is configured to be symmetrical (or substantially symmetrical) such that it can be deployed the same way using either the jugular or the femoral approach. It may also be advantageous to have the retrieval member 26, 28 positioned centrally in the deployed blood vessel such that a recovery device can easily locate and engage the slidable members 22, 24.

The slidable members 22, 24 allow a physician to approach the deployed vessel filter from either direction and collapse the filter legs 30, 32 on the corresponding side of the vessel filter 2 such that the vessel filter 2 can be captured within a recovery sheath and retrieved from the patient's body. A snare located at the distal end of a flexible rod which is inserted within the lumen of the recovery sheath may be utilized to engage the retrieval member and displace the slidable member. The displacement of the slidable member toward the tips of the filter legs forces the filter legs to collapse toward a longitudinal axis of the vessel filter. Once the filter legs adjoining the recovery sheath have been collapsed, the vessel filter can either be pulled into the recovery sheath or the recovery sheath can be advanced distally to capture the vessel filter within the lumen of the recovery sheath. The distally positioned filter legs are compressed as the recovery sheath is advanced beyond the welded tube. As one skilled in the art having the benefit of this disclosure would appreciate, different materials, joining methods, and configurations may be implemented in manufacturing the vessel filter.

In another variation, the slidable member is attached to the delivery system rather than the implanted vessel filter itself. The delivery system includes a slidable member attached to an extendable member of the delivery system. To retrieve the deployed vessel filter, the extendable member is advanced toward the deployed vessel filter and the slidable member is placed over the deployed vessel filter. The extendable member is then retracted, forcing the slidable member to compress the vessel filter legs adjoining the extendable member and forcing these filter legs to collapse. A recovery sheath may then be utilized to capture the partially collapsed vessel filter. In one variation, the slidable member is configured with an adjustable structure allowing it to transform between the shapes of "C" and "O" to surround the struts. For example, an opened "C" shaped may allow the placement of the slidable member over the welded tube 12 on the vessel filter 2 shown in FIG. 1A. Once the slidable member is positioned on the welded tube, the opening on the slidable member is closed up to form an "O" shape around the welded tube. The slidable member is then displaced toward the proximal direction to compress the expanded filter legs at the proximal end of the vessel filter.

Figure 2:
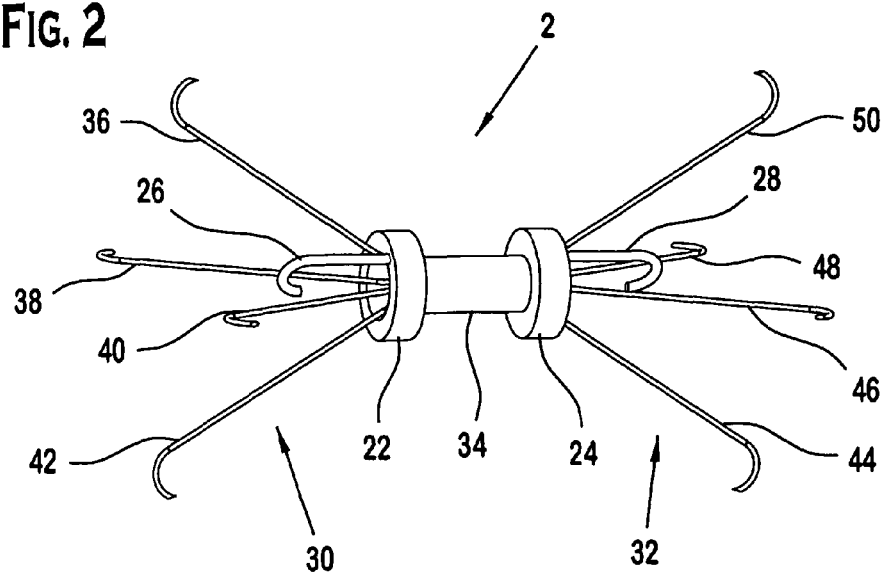
FIG. 2 is a perspective view of another variation of the vessel filter comprising a connecting member supporting a first set of flexible wiring extending radially from the proximal end of the connecting member, and a second set of flexible wiring extending radially from the distal end of the connecting member. Two slidable members are disposed over the length of the vessel filter for compressing the radially expanded wirings.
Figure 3:
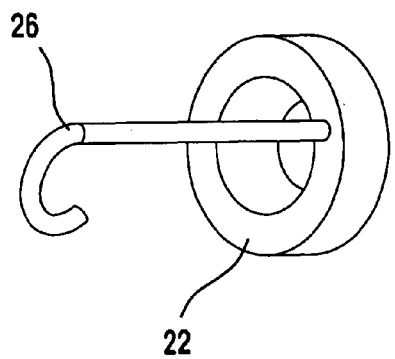
FIG. 3 illustrates one of the slidable members from FIG. 2.

In another variation, the vessel filter includes two sets of filter legs 30, 32 extending from both ends of a connecting member 34, as shown in FIG. 2. In one example, the connecting member 34 includes a short rod. A first set 30 of four filter legs 36, 38, 40, 42 extend radially from the proximal end of the connecting member 34 and away from the longitudinal axis of the vessel filter 2, and a second set 32 of four filter legs 44, 46, 48, 50 extend radially from the distal end of the connecting member 34 and away from the longitudinal axis of the vessel filter. Two ring-shaped slidable members 22, 24 are disposed over the connecting member 34. The proximally positioned slidable member 22 can be displaced in the proximal direction to force the first set 30 of the filter legs 36, 38, 40, 42 to collapse, and the distally positioned slidable member 24 can be displaced in the distal direction to force the second set 32 of filter legs 44, 46, 48, 50 to collapse. As shown in FIG. 3, each of the slidable members 22, 24 is configured with a retrieval member 26. In this example, each of the retrieval members 26, 28 have a hook-like configuration, although in other embodiments the retrieval member may have other configurations as known to one skilled in the art.

Figure 4:
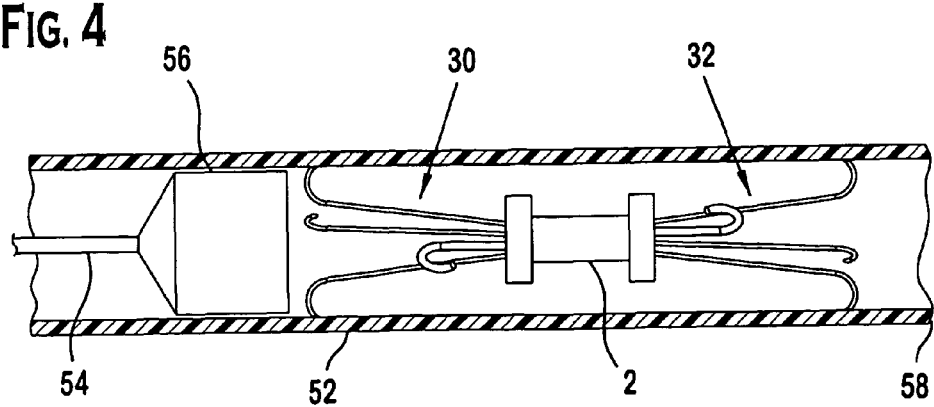
FIG. 4 illustrates one variation of a deployment system for placement of a vessel filter including an integrated compression mechanism.

Various methods that are well known to one skilled in the art may be utilized to deploy the vessel filter. One example is illustrated in FIG. 4. The vessel filter 2 with an integrated compression mechanism is positioned within a delivery sheath 52. A pusher rod 54 including a pusher pad 56 is slidably positioned within the lumen of the delivery sheath 52 immediately proximal of the vessel filter 2. An introducer sheath may be inserted into the target vessel with the assistance of a guidewire. Once the distal end of the introducer sheath is positioned at the intended deployment location, the guidewire is removed and the delivery sheath 52 carrying the vessel filter 2 is advanced into the target vessel through the introducer sheath. Once the distal end 58 of the delivery sheath 52 is advanced beyond the distal end of the introducer sheath, the physician may then deploy the vessel filter by holding the pusher wire 54 in place while simultaneously retracting the delivery catheter along with the introducer sheath to expose the vessel filter 2. Without the compressing force provided by the delivery sheath 52, the legs 30, 32 on the vessel filter 2 expand radially and engage the blood vessel wall.

To retrieve the deployed vessel filter, a guidewire may be used to introduce a recovery sheath into the blood vessel. An elongated member may be inserted into the recovery sheath to engage the retrieval member and displace the corresponding slidable member in order to collapse the filter legs on the vessel filter. For example, a recovery sheath 60 is advanced into the vessel until the distal end 62 of the recovery sheath 60 is next to the deployed vessel filter 2, as shown in FIG. 5A. A flexible rod 64 with a snare 66 is inserted into the recovery sheath 60. The snare 66 is placed on the retrieval member 26 to engage the slidable member 22. The flexible rod 64 is then retracted pulling the slidable member 22 toward the distal end 62 of the recovery sheath 60, causing the corresponding filter legs 30 to collapse, as shown in FIG. 5B. With the proximal portion of the vessel filter compressed, the recovery sheath 60 is advanced in the distal direction. As the recovery sheath 60 advances beyond the mid-section 68 of the vessel filter 2, the distal tip 62 of the recovery sheath engages the filter legs 32 at the distal end of the filter 2 and forces these filter legs 32 to collapse toward the longitudinal axis of the vessel filter, disengaging the legs 32 from the blood vessel wall, as shown in FIG. 5C. Once the vessel filter 2 is completely contained within the lumen of the recovery sheath 60, the physician may withdraw the recovery sheath 60 along with the captured vessel filter 2 from the body of the patient.

In vessel filter designs where both the distal filter legs and the proximal filter legs include hooks having tips that curve toward the mid section of the vessel filter body, the vessel filter retrieving technique illustrated in FIG. 5B may be particularly advantageous. As the user pulls the slidable member 22 towards the proximal direction, the distal end hooks 33 dig into the blood vessel wall since the tips of the hooks are curved in the proximal direction. As a result, the distal hooks 33 prevent the vessel filter 2 from moving proximally. The displacement of the slidable member 22 forces the proximal filter legs 30 to collapse and pulling the proximal hooks 31 out of the blood vessel wall. Since, in this variation, the tips of the proximal hooks 31 are curved in the distal direction, the pulling force in the proximal direction may easily disengage the proximal hooks 31 from the blood vessel wall. As a result, less force is required to collapse the proximal filter legs.

In another variation of a vessel filter recovery system, a restraining member is provided to maintain the position of the deployed vessel filter when the slidable member is being displaced along the length of the deployed vessel filter. In one example, a snare 66 is used to engage the retrieval member 26. With the snare 66 engaging the vessel filter 2, the recovery sheath 60 is advanced along the rod 67, which supports the snare. Since the distal end of the rob 67 is coupled to the vessel filter 2 through the snare 66, as the recovery sheath 60 is advanced towards the vessel filter, the distal end 61 of the recovery sheath 60 will center itself in relation to the vessel filter 2. Once the distal end 61 of the recovery sheath 60 is positioned adjacent to the vessel filter 2, the user can then advance a restraining member 70 towards the deployed vessel filter 2 until the distal end of the restraining member 70 abuts the vessel filter 2, as shown in FIG. 6. With the restraining member 70 holding the vessel filter 2 in place, the user pulls the slidable member 22 towards the recovery sheath 60, which in turn causes the legs 30 of the vessel filter 2 to collapse. Once all the proximal legs 30 have collapsed, the vessel filter 2 can then be pulled into the recovery sheath 60. In another approach, once all the proximal legs 30 have collapsed, the recovery sheath 60 is advanced distally to capture the vessel filter 2.

In another variation, a stopper is implemented on the vessel filter to prevent the slidable member from disengaging from the struts or legs of the vessel filter. For example, a stopper may be placed at the distal end of one of the vessel filter legs to capture the slidable member and prevent the slidable member from moving beyond the length of the filter leg. In one particular design, stoppers 72, 74, 76, 78 are positioned at the tip portion of each of the filter legs 80, 82, 84, 86, as shown in FIG. 7. The user engages the slidable member 22 and displaces it toward the tip of the filter legs to collapse the filter legs 80, 82. Once the slidable member reaches the tip portion of the filter legs, the stoppers 72, 74 engage the slidable member 22 and prevent the slidable member 22 from further displacement. The stopper may also be configured to allow the user to apply enough lateral force on the vessel filter to drag the vessel filter into the lumen of the recovery sheath.

FIG. 8A illustrates another variation of a vessel filter 2. In this example, the vessel filter is not fully symmetrical. This filter is configured such that it can be delivered using both the jugular and the femoral approach. However, depending on the orientation of the deployment, the filter may be removed using only one of the jugular or the femoral approach. An elongated body 88 (e.g., a center post) coupled to the slidable member 22 is slidably positioned through the mid-portion of the vessel filter 2. A stop 92 is positioned at the proximal end of the elongated body 88. As the slidable member 22 is displaced distally, the elongated body 88 slides through the mid-section 90 of the vessel filter 2 toward the distal end of the vessel filter until the stop 92 engages the mid-portion 90 of the vessel filter, and the slidable member 22 is prevented from further displacement in the distal direction, as shown in FIG. 8B.

In one design, a recovery member 94 connected to the slidable member 22 has an elongated portion 88 that extends through the slidable member 22. The distal end 96 of the recovery member 94 is in the form of a curved-shape retrieval member and the proximal end 98 has an enlarged bulb which forms a stop 92. The mid-portion 90 of the filter includes a cylindrical body 100 which includes a central lumen 102 allowing the elongated portion 88 to be slidably displaced within, and peripheral orifices 104, 106, 108, 110, 112, 114, 116, 118, 120 to secure the struts 4, 6 on the cylindrical body 100, as illustrated in FIG. 8C. In another design, the mid-portion of the filter includes a first small diameter tube (e.g., a nitinol tube, etc.) positioned between the struts so that the recovery member 94 can slide therewithin. A second tube with a larger diameter is positioned around the struts to hold the struts in place. In other variations, the curved shaped retrieval member may be replaced with other interfacing structures to allow the user to engage the slidable member 22 and the recovery member 94.

Figure 9A:
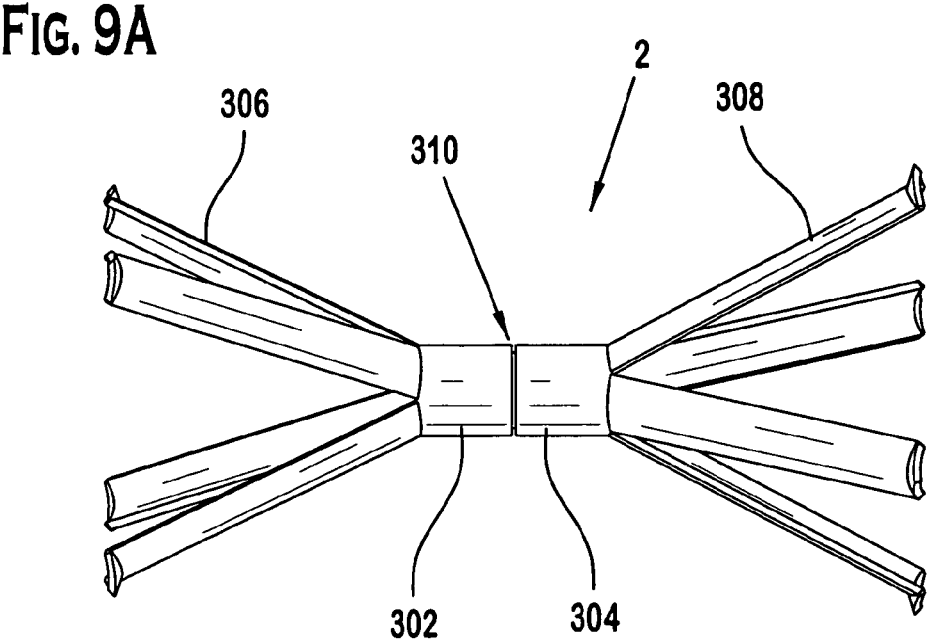
FIG. 9A shows a side view of one variation of a vessel filter, where the legs of the filter are cut from tubings which are coupled to each other to form the shaft of the filter.
Figure 9B:
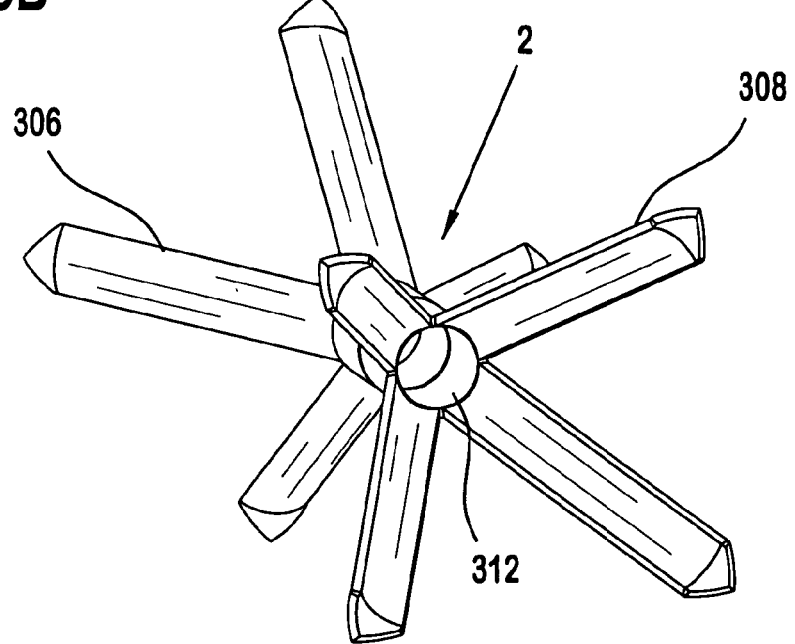
FIG. 9B is a perspective view of the vessel filter of FIG. 9A.

In yet another variation, the underlying filter structure is cut from a tube (e.g., nitinol) and the legs of the filter are derived from the two ends of the tube, and then formed to achieve a final shape. A slidable member is then inserted onto the pre-cut structure to form the vessel filter. The slidable member may include a retrieval member such that the user can easily engage the slidable member to collapse the filter legs at one end of the vessel filter. In one example, as shown in FIG. 9A, the vessel filter 2 includes two tubings 302, 304 coupled to each other. The outer ends of the tubings 306, 308 are pre-cut to form the filter legs. The inner ends of the tubing are coupled together to form the shaft 310 of the vessel filter. As shown in FIG. 9B, in this example, the two tubings 302, 304 are connected to each other through an interconnecting member 312 positioned within the lumen of the tubings. The two tubings 302, 304 may also be welded together or coupled to each other through other methods that are well know to one skilled in the art. One or more slidable members may be disposed over the shaft 310 of the vessel filter to provide the mechanism to selective collapse the filter legs at the outer ends 306, 308 of the vessel filter. For example, a tubular structure may be slidably positioned over the shaft 310 of the vessel filter. The tubular structure may include a retrieval member such the user can engage the tubular structure to collapse the filter legs on one end of the vessel filter.

Figure 10A:
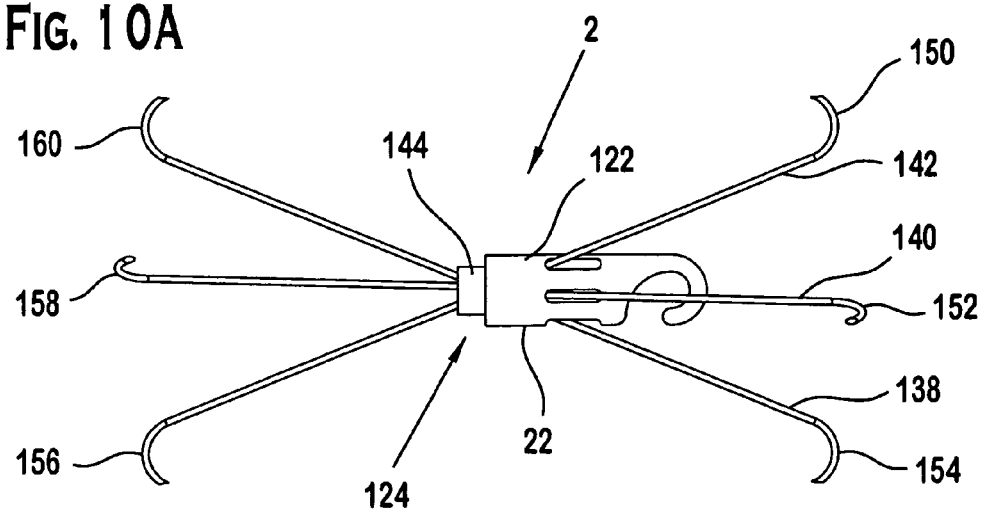
FIG. 10A illustrates another variation of a vessel filter where the slidable member includes a tubular structure with slots to accommodate the radially expanding struts at the distal end of the vessel filter.

In another variation, illustrated in FIG. 10A, the slidable member 22 includes a tubular body 122 positioned around the mid-section 124 of an underlying vessel filter structure. Slots 126, 128, 130, 132, 134, 136 are provided on the tubular body 122 to allow the struts 138, 140, 142 or legs to pass through the tubular body 122. As shown in FIG. 10A, struts 138, 140, 142 are threaded through slots 126, 128, 130 on the wall of a tubular body 122. The struts 138, 140, 142 assume their pre-designed shape (i.e., expanded position) when the tubular body 122 is in the position shown in FIG. 10A. When the tubular body 122 is displaced in the distal direction relative to the coupling member 144, the portion of the struts extending distally through the tubular body collapse toward the longitudinal axis of the vessel filter 2. Once the distal struts are collapsed, a recovery sheath can then be utilized to capture the vessel filter 2.

Figure 10B:
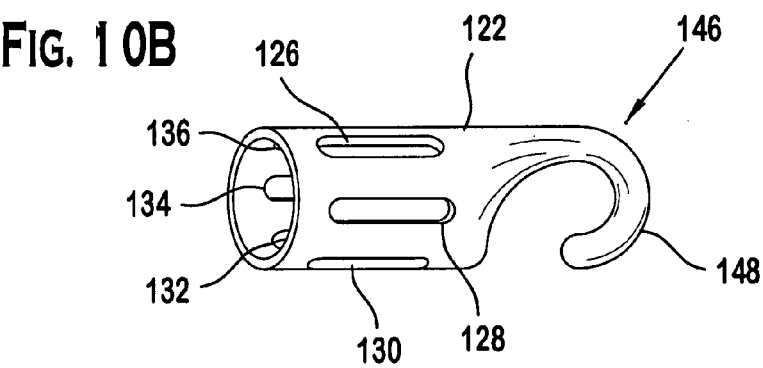
FIG. 10B is perspective view illustrating the slidable member from FIG. 10A.

FIG. 10B shows one possible configuration of the tubular body 122 where elongated slots 126, 128, 130, 132, 134, 136 are positioned around the circumferential surface of the tubular body 122, and the distal end 146 of the tubular body 122 is configured with a retrieval member 148. In one variation, the hooks on the distal legs 150, 152, 154 may be configured such that they are less sharp than the hooks 156, 158, 160 on the proximal legs to allow for easier disengagement of the distal legs 150, 152, 154 from the vessel wall.

Figure 10C:
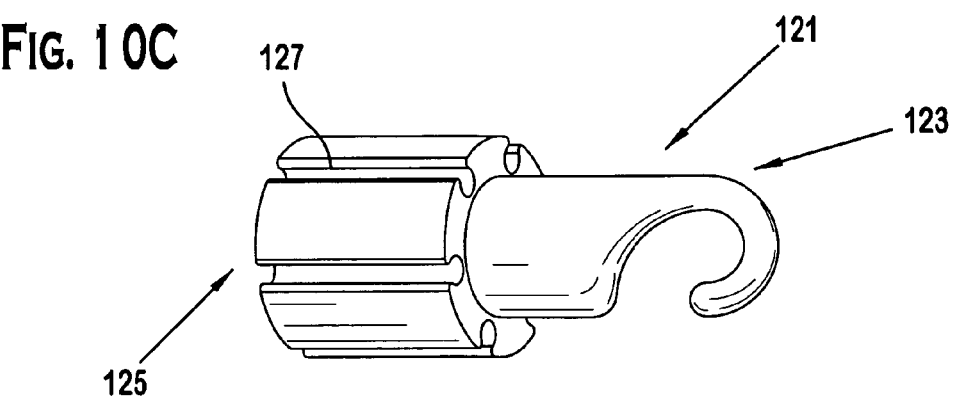
FIG. 10C is a perspective view of another embodiment of a slidable member.
Figure 10D:
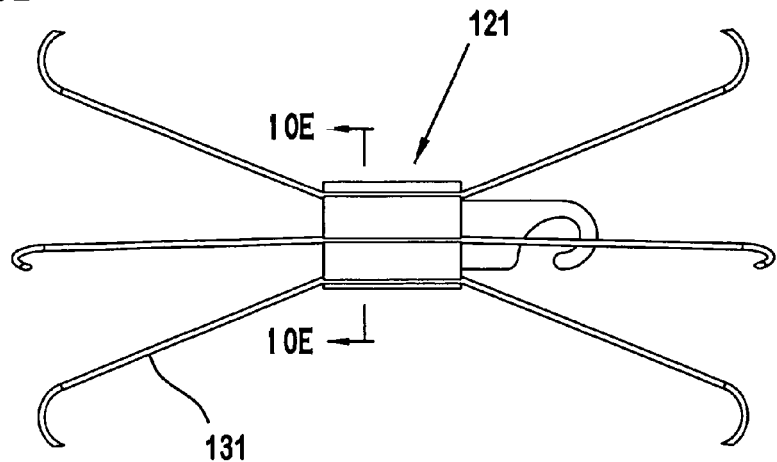
FIG. 10D is a perspective view of the slidable member of FIG. 10C with struts positioned through the slots of the slidable member to form a vessel filter.
Figure 10E:
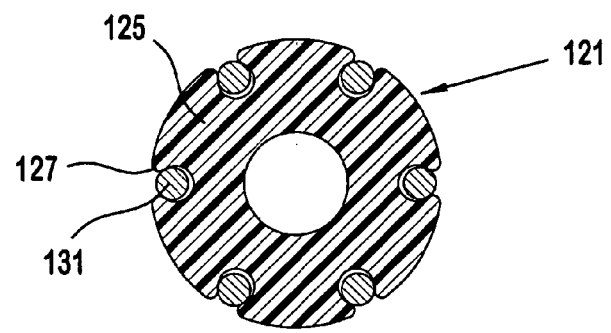
FIG. 10E is a cross-sectional view of the vessel filter of FIG. 10D.

FIGS. 10C-10E illustrate an embodiment of a vessel filter in which sliding member 121 includes a retrieval member 123 and a base member 125 with slots 127 spaced about the circumference of the base member 125. In this embodiment, the slots 127 are formed in the base member 125 with an open section along the outer surface of the base member 125 to permit the struts 131, positioned therein, greater freedom of movement; however, the open sections have a width smaller than the width (e.g., diameter) of the struts 131 to prevent movement of the struts 131 out of the slots 127. Thus, different than other filter embodiments, the sliding member 121 does not completely surround the struts 131. Although the open sections of the slots 127 are shown along the entire length thereof in FIG. 10C, in other embodiments, the slots 127 may include one or more open sections along their length to facilitate freedom of movement for the struts 131. Moreover, depending on the cross-sectional shapes of the struts 131, the slots 127 may be shaped differently than the "C" shaped cross-section of FIG. 10C. For example, if the struts had a square, triangular or rectangular cross-sectional shape, the cross-section of the slots 127 would be formed accordingly to accommodate the struts 131 and facilitate sliding movement therethrough while preventing movement of the struts 131 out of the slots 127. FIG. 10D shows the sliding member 121 with a set of struts 131 positioned through the slots 127. As discussed above with reference to FIG. 10A, the displacement of the sliding member 121 in a distal direction results in the collapse of the distally extending portion of the struts 131 toward the longitudinal axis of the vessel filter. FIG. 10E is a cross-sectional view through the base member 125, showing a cross-section of the slots 127 and struts 131. Although not shown, in one embodiment, the vessel filter of FIG. 10D includes a coupling member as described herein. It should be appreciated that the struts 131 may include hooks on the ends thereof as discussed herein.

Moreover, although the distally extending portion of the struts 131 of the vessel filter are shown in FIG. 10D to diverge (extend radially outward) from the longitudinal axis of the vessel filter at a generally common location along the longitudinal axis of the vessel filter (i.e., from a distal end of slots 127 in the base member 125) and at a generally similar angle with respect to the longitudinal axis of the vessel filter, other possibilities for divergent locations and angles are contemplated herein. For example, the distally extending portion of the struts 131 may diverge from the longitudinal axis at two or more locations. In one embodiment, a first set of two or more of the distally extending portion of the struts 131 diverge from the distal end of the slots 127 at a first angle and a second set of two or more of the distally extending portion of the struts 131 diverge at a location distal to the sliding member 121 at a second angle less than the first angle. This configuration results in sequential deployment and recovery of the vessel filter. In particular with respect to recovery, as sliding member 121 is moved distally along the longitudinal axis of the vessel filter, the first set of the distally extending portion of the struts 131 are collapsed toward the longitudinal axis of the vessel filter and subsequently, as the sliding member is moved further distally, the second set of the distally extending portion of the struts 131 are collapsed toward the longitudinal axis of the vessel filter. It should be appreciated that there may be more than two sets of divergent strut portions (i.e., more than two divergent locations) and that the angles of divergence may be substantially equivalent, greater in a distal direction, smaller in a distal direction, or varying along the length of the vessel filter. In addition, the proximally extending portion of the struts may also have sets of strut portions that diverge at different locations and/or at different angles with respect to the longitudinal axis of the vessel filter.

Figure 11:
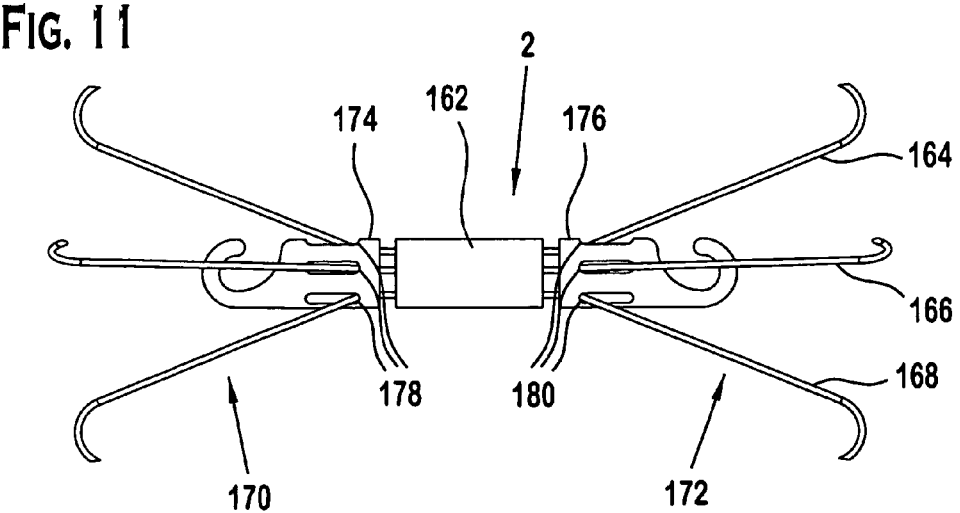
FIG. 11 illustrates another variation where the vessel filter includes two slidable members with built-in slots to accommodate the expandable filter legs.

In another variation, the vessel filter includes a coupling member 162 holding together struts 164, 166, 168 to form a set of proximal filter legs 170 extending proximally from the coupling member 162, and a set of distal filter legs 172 extending distally from the coupling member 162, as shown in FIG. 11. A first slidable member 174 is positioned over the proximal legs 170. Slots 178 are provided on the slidable member to allow the filter legs 170 to pass through. A second slidable member 176 is positioned over the distal legs 172. Slots 180 are provided on the second slidable member 176 to allow the distal filter legs 172 to pass through. Displacement of the slidable members 174, 176 allows the user to electively compress the distal 172 and/or the proximal 170 filter legs.

Figure 12:
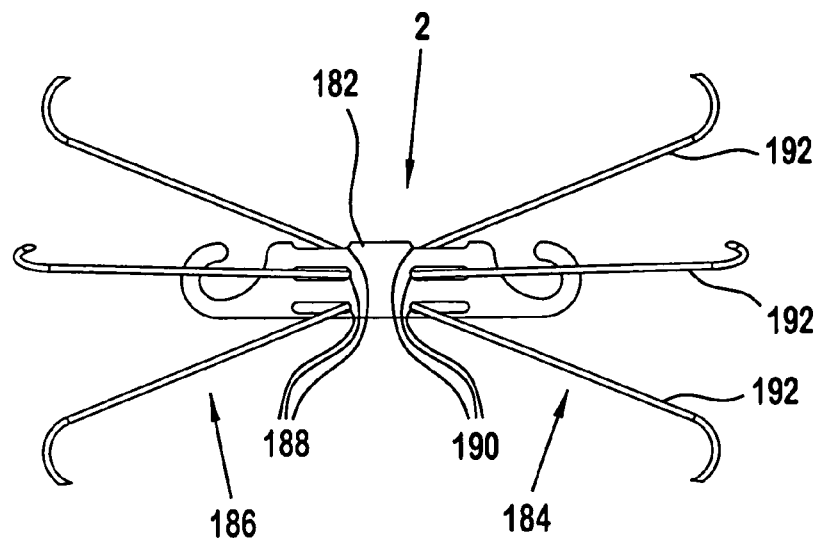
FIG. 12 illustrates yet another variation where a single slidable member is configured with two sets of slots to accommodate the expandable filter legs at both the distal and the proximal end of the device.

In another variation, a single slidable member 182 is provided to allow the user to electively compress either the distal legs 184 or the proximal legs 186 on a vessel filter 2. In one example illustrate in FIG. 12, a single slidable member 182 is configured with two sets of slots 188, 190 to accommodate the expandable filter legs 184, 186 at both the distal and the proximal end of the device. When the slidable member 182 is displaced in the distal direction relative to the struts 192, the edge of the distal slots 190 forces the distal legs 184 to collapse toward the longitudinal axis of the vessel filter 2. When the slidable member 182 is displaced in the proximal direction relative to the struts 192, the edge of the proximal slots 188 forces the proximal legs 186 to collapse toward the longitudinal axis of the vessel filter 2. In one design, the struts 192 are not joined together. Instead, the struts 192 are coupled to the slidable member, which holds the struts together. The struts 192 may be moveable in relation to each other. In another design, a coupling member is placed at the midsection of the struts 192 to couple the struts to each other.

Figure 13A:
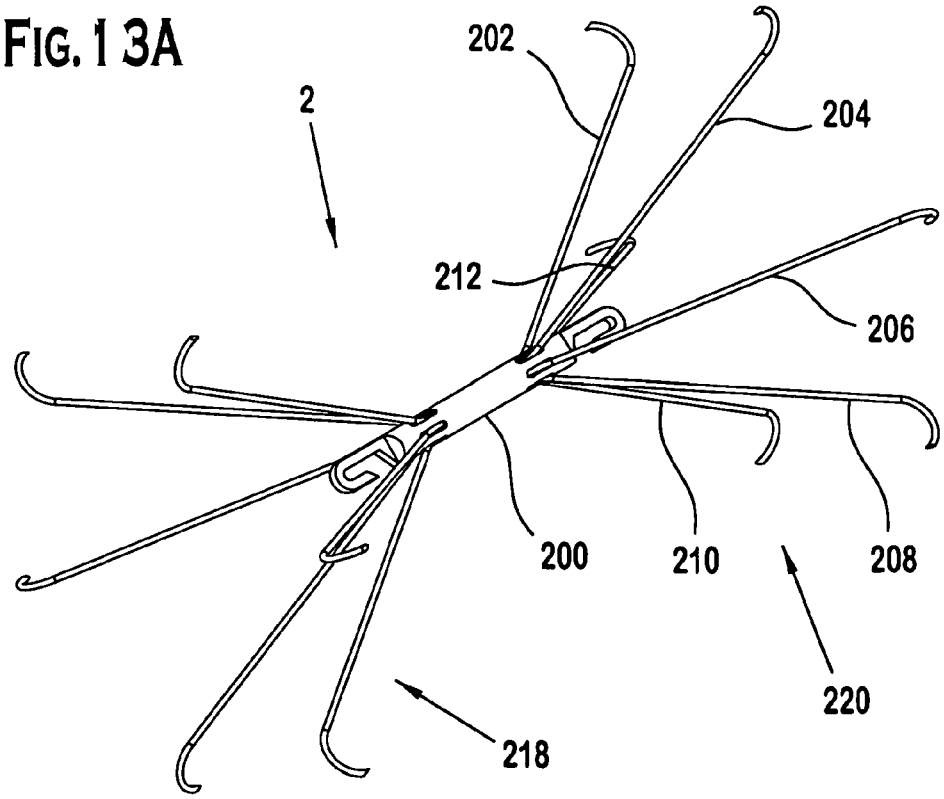
FIG. 13A is a perspective view illustrating another variation of a vessel filter with an integrated filter leg compression mechanism.
Figure 13B:
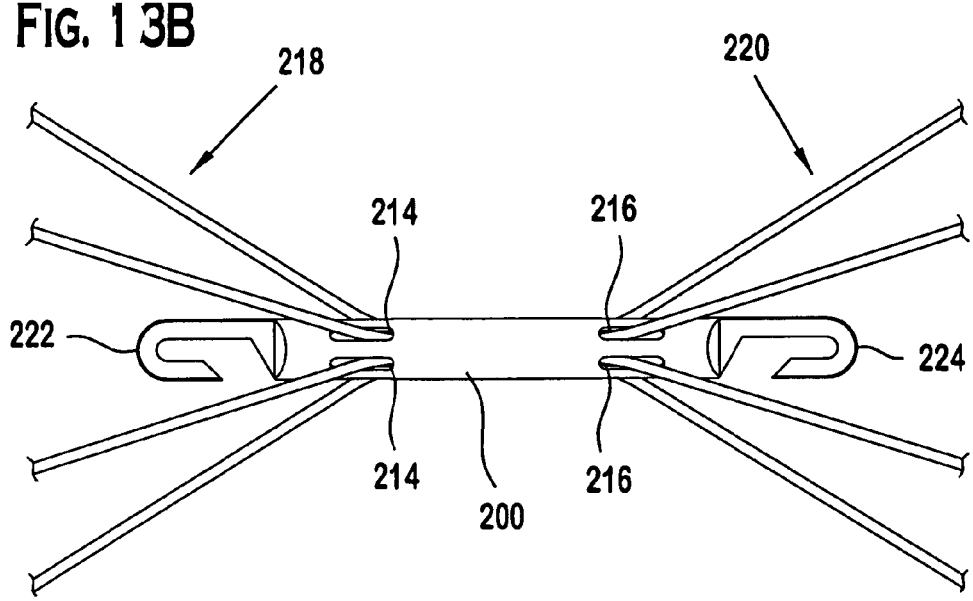
FIG. 13B is a close-up expanded view of the mid-section of the vessel filter of FIG. 13A.
Figure 13C:
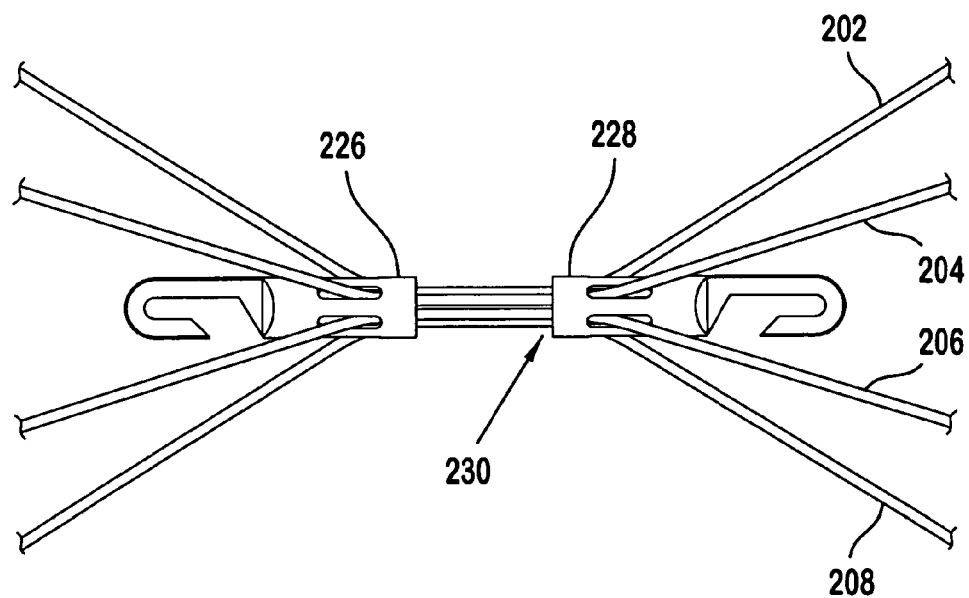
FIG. 13C shows the vessel filter of FIG. 13B with the slidable member being partially disassembled to expose the struts at the mid-section of the device for illustration purposes.
Figure 13D:
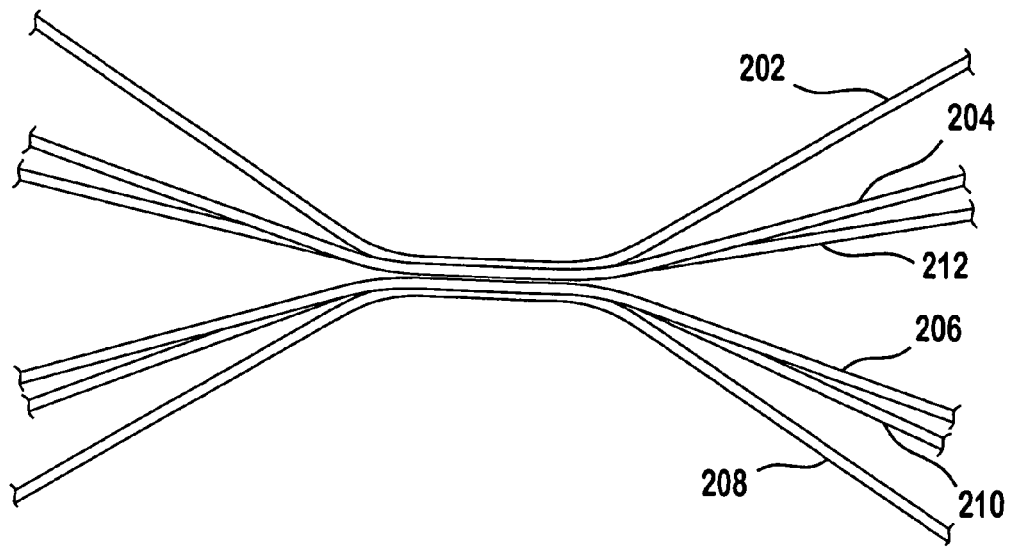
FIG. 13D illustrates the configuration of the struts in the vessel filter of FIG. 13B. The vessel filter is shown without the slidable member for illustration purposes.

FIG. 13A illustrates another variation of the vessel filter 2 comprising six struts 202, 204, 206, 208, 210, 212 coupled together with a slidable member 200. The slidable member 200 includes an elongated structure with a lumen to allow the struts to pass through. A first set of slots 214 is provided on the proximal portion of the slidable member 200 to allow the proximal portions of the struts to form the proximally expanding filter legs 218. A second set of slots 216 is provided on the distal portion of the slidable member 200 to allow the distal portions of the struts to form the distally expanding filter legs 220, as shown in FIG. 13B. Retrieval members 222, 224 are provided on both the distal end and the proximal end of the elongated body 200. The user may engage the retrieval members 222, 224 to displace the slidable member 200 in either the distal or the proximal direction, and thus selectively collapse the corresponding set of the filter legs 218, 220. FIG. 13C shows a partially disassembled elongated body 226, 228, illustrating the position of the struts 202, 204, 206, 208, 210, 212 within the lumen 230 of the elongated body 200. FIG. 13D shows the configuration of the struts 202, 204, 206, 208, 210, 212 in FIG. 13B with the slidable member 200 removed to expose the struts 202, 204, 206, 208, 210, 212.

Figure 14:
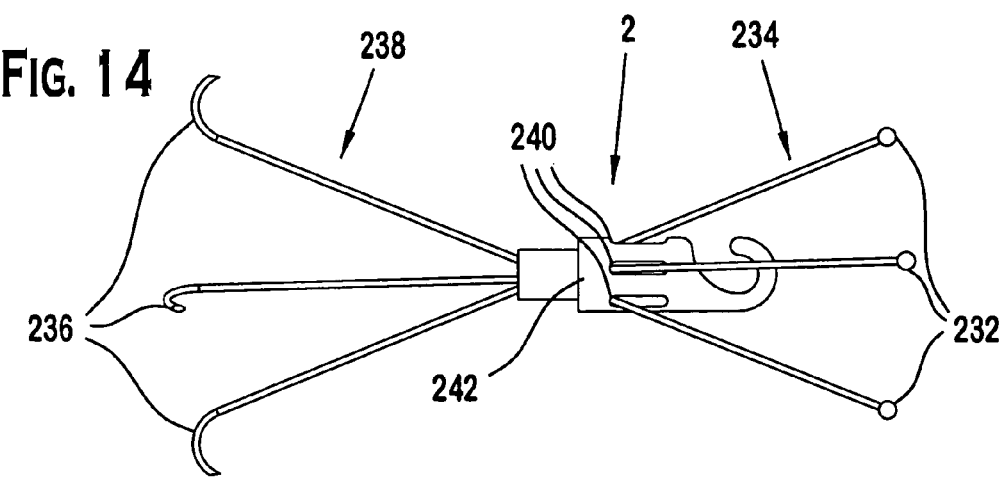
FIG. 14 illustrates another variation of the vessel filter where one set of vessel filter legs is configured with elastic hooks while the other set of the vessel filter legs are modified to allow easy disengagement from the blood vessel wall. The distal ends of the filter legs may be larger than the corresponding slots on the slidable member to prevent the slidable member form dislodging from the vessel filter legs.

In one embodiment of the present invention, it is contemplated that the distal legs and the proximal legs may have different shapes. In one design variation, the tips 232 of the distal legs 234 are rounded while the tips 236 of the proximal legs 238 are configured with elastic hooks. One example of such a configuration is shown in FIG. 14. The rounded tips 232 may be configured with a bulging structure such that they are larger than the slots 240 on the tubular body to prevent the slidable member 242 from dislodging from the distal legs 234.

Figure 15:
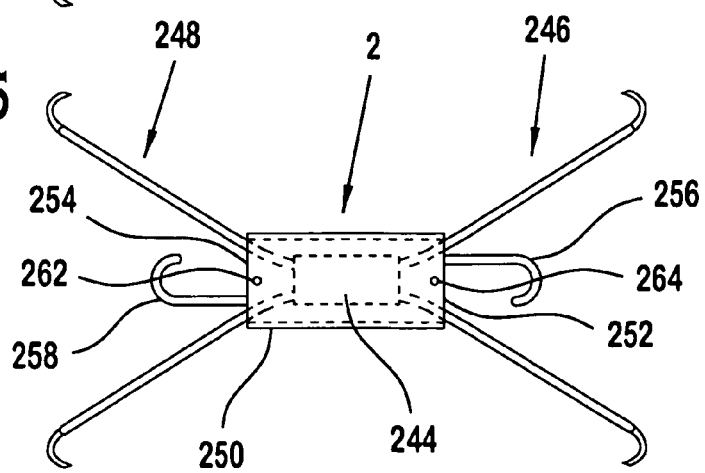
FIG. 15 illustrates another variation of the vessel filter where a single elongated slidable member is disposed over the struts. The elongated slidable member is configured such that it may be utilized to compress either the distal or the proximal set of filter legs depending on the direction of the displacement.

In yet another variation, the filter 2 includes a connecting member 244 with legs 246, 248 extending both distally and proximally, as shown in FIG. 15. A tubular structure 250 is slidably disposed over the connecting member 244 to serve as the slidable member. The legs 246, 248 exit the tubular structure 250 through the distal 252 and the proximal 254 openings. Retrieval members 256, 258 may be provided on the tubular structure 250 to allow the user to engage the tubular structure 250. When the tubular structure 250 is slid in the distal direction, the distal filter legs 246 collapse. When the tubular structure 250 is slid in the proximal direction, the proximal filter legs 248 collapse. The tubular structure 250 may be coupled to the connecting member 244 to prevent the tubular structure from sliding too far in one direction and dislodging from the filter legs. For example, stops 262, 264 may be provided in the lumen of the tubular structure to prevent over-sliding.

Each of the filter embodiments discussed herein can also include one or more filaments attached thereto. In one embodiment, the filaments are made of suture material, although in other embodiments, the filaments are made of a bio-resorbable material or any of the materials discussed above with respect to possible materials for the filter. The filaments could be attached to the body, one or more of the appendages of the filter, or a combination thereof. The filaments may be attached to the filter by wrapping the filament one or more times around an attachment location on the filter, tying the filament to an attachment location on the filter, heating the filament adjacent to an attachment location on the filter to create a bond therebetween, applying an adhesive to the filament and/or an attachment location on the filter, applying a solvent to the filament and/or an attachment location on the filter, etc. Of course, other possibilities for attaching the filament to an attachment location on a filter known to one skilled in the art are also within the scope of this invention.

This invention has been described and specific examples of the invention have been portrayed. While the invention has been described in terms of particular variations and illustrative figures, those of ordinary skill in the art will recognize that the invention is not limited to the variations or figures described. In addition, where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially as described above. Therefore, to the extent there are variations of the invention, which are within the spirit of the disclosure or equivalent to the inventions found in the claims, it is the intent that this patent will cover those variations as well. Finally, all publications and patent applications cited in this specification are herein incorporated by reference in their entirety as if each individual publication or patent application were specifically and individually put forth herein.

What is claimed is:

1. An implantable vascular device, comprising:
a first compressible filter including a first set of struts expanding radially away from a filter longitudinal axis in a proximal direction, each strut of the first set of struts including a stopper positioned adjacent an end thereof;
a second compressible filter including a second set of struts expanding radially away from the longitudinal axis in a distal direction, each strut of the second set of struts including a stopper positioned adjacent an end thereof;
a first slidable member disposed over at least the first set of struts, the first slidable member including a first body having an outer perimeter, the first set of struts disposed radially inside the outer perimeter of the first body, the first slidable member further including a first recovery member extending from the first body in a proximal direction; and
a second slidable member disposed over at least the second set of struts, the second slidable member including a second body having an outer perimeter, the second set of struts disposed radially inside the outer perimeter of the second body, the second slidable member further including a second recovery member extending from the second body in a distal direction,
wherein at least one of the first and second slidable members comprises a tubular structure including a plurality of channels, at least one of the first and second set of struts having each strut disposed in a corresponding channel of the plurality of channels.

2. The vascular device according to claim 1, wherein the first slidable member includes a first set of channels and the second slidable member includes a second set of channels, each of the first set of struts disposed in a corresponding channel of the first set of channels, and each of the second set of struts disposed in a corresponding channel of the second set of channels, the stopper of each of the first set of struts and second set of struts having a cross-sectional area greater than the channels of the first and second set of channels.

3. The vascular device according to claim 1, wherein each of the struts of the first set of struts and second set of struts includes a hook extending therefrom.

4. The vascular device according to claim 3, wherein each hook includes an elastic structure with a generally arcuate configuration in an operative condition and a generally linear configuration in a constrained condition.

5. The vascular device according to claim 3, wherein each hook has a cross-sectional area less than a cross-sectional area of the strut from which it extends.

6. The vascular device according to claim 1, wherein the first set of struts are coupled to the second set of struts.

7. A vessel filter, comprising:
a plurality of struts, a proximal portion of the plurality of struts forming a first collapsible cone expanding radially outward in a proximal direction, a distal portion of the plurality of struts forming a second collapsible cone expanding radially outward in a distal direction, each strut including a proximal hook extending from a proximal end and a distal hook extending from a distal end, each strut further including a proximal stopper positioned adjacent the proximal hook and a distal stopper positioned adjacent the distal hook;
a first slidable member disposed over the plurality of struts, the first slidable member including a first set of channels, each of the plurality of struts disposed in a corresponding channel of the first set of channels, the first slidable member further including a first recovery member extending in a proximal direction; and
a second slidable member disposed over the plurality of struts, the second slidable member including a second set of channels, each of the plurality of struts disposed in a corresponding channel of the second set of channels, the second slidable member further including a second recovery member extending in a distal direction, each proximal stopper and distal stopper having a cross-sectional area greater than each of the channels of the first set of channels and the second set of channels.

8. The vessel filter according to claim 7, wherein each hook includes an elastic structure with a generally arcuate configuration in an operative condition and a generally linear configuration in a constrained condition.

9. The vessel filter according to claim 7, wherein each hook has a cross-sectional area less than a cross-sectional area of the strut from which it extends.

10. An implantable vascular device, comprising:
a first compressible filter including a first set of struts expanding radially away from a filter longitudinal axis in a proximal direction, each strut of the first set of struts including a stopper positioned adjacent an end thereof;
a second compressible filter including a second set of struts expanding radially away from the longitudinal axis in a distal direction, each strut of the second set of struts including a stopper positioned adjacent an end thereof;
a first slidable member disposed over at least the first set of struts, the first slidable member including a first body having an outer perimeter, the first set of struts disposed radially inside the outer perimeter of the first body, the first slidable member further including a first recovery member extending from the first body in a proximal direction; and
a second slidable member disposed over at least the second set of struts, the second slidable member including a second body having an outer perimeter, the second set of struts disposed radially inside the outer perimeter of the second body, the second slidable member further including a second recovery member extending from the second body in a distal direction,
wherein the first slidable member includes a first set of channels and the second slidable member includes a second set of channels, each of the first set of struts disposed in a corresponding channel of the first set of channels, and each of the second set of struts disposed in a corresponding channel of the second set of channels, the stopper of each of the first set of struts and second set of struts having a cross-sectional area greater than the channels of the first and second set of channels.

11. The vascular device according to claim 10, wherein at least one of the first and second slidable members comprises a tubular structure.

12. The vascular device according to claim 10, wherein each of the struts of the first set of struts and second set of struts includes a hook extending therefrom.

13. The vascular device according to claim 12, wherein each hook includes an elastic structure with a generally arcuate configuration in an operative condition and a generally linear configuration in a constrained condition.

14. The vascular device according to claim 12, wherein each hook has a cross-sectional area less than a cross-sectional area of the strut from which it extends.

15. The vascular device according to claim 10, wherein the first set of struts are coupled to the second set of struts.

* * * * *